United States Patent
Shin

(10) Patent No.: US 9,868,028 B2
(45) Date of Patent: Jan. 16, 2018

(54) VIRTUAL REALITY INDOOR BICYCLE EXERCISE SYSTEM USING MOBILE DEVICE

(71) Applicant: CONSIDERC INC., Ansan-si, Gyeonggi-do (KR)

(72) Inventor: Jaehyun Shin, Seoul (KR)

(73) Assignee: CONSIDERC INC., Ansan-si, Gyeonggi-do (KR)

( * ) Notice: Subject to any disclaimer, the term of this patent is extended or adjusted under 35 U.S.C. 154(b) by 6 days.

(21) Appl. No.: 15/034,525

(22) PCT Filed: Sep. 3, 2014

(86) PCT No.: PCT/KR2014/008277
§ 371 (c)(1),
(2) Date: May 4, 2016

(87) PCT Pub. No.: WO2015/034265
PCT Pub. Date: Mar. 12, 2015

(65) Prior Publication Data
US 2016/0325146 A1    Nov. 10, 2016

(30) Foreign Application Priority Data

Sep. 4, 2013   (KR) .................. 10-2013-0106053
Sep. 16, 2013  (KR) .................. 10-2013-0110932

(51) Int. Cl.
*A63B 21/005*   (2006.01)
*A63B 22/06*    (2006.01)
(Continued)

(52) U.S. Cl.
CPC .... *A63B 24/0087* (2013.01); *A63B 21/00069* (2013.01); *A63B 21/22* (2013.01);
(Continued)

(58) Field of Classification Search
CPC . A63B 24/0087; A63B 71/0622; A63B 21/22; A63B 21/00069; A63B 21/4035;
(Continued)

(56) References Cited

U.S. PATENT DOCUMENTS 2,450,979 A * 10/1948 Moller .................... B62H 1/12
                                                         280/293
3,686,776 A *  8/1972 Dahl ..................... G09B 9/058
                                                          434/61
(Continued)

FOREIGN PATENT DOCUMENTS

JP        3064889 U         10/1999
KR   20-1999-0033624 U      8/1999
(Continued)

*Primary Examiner* — Stephen R Crow
*Assistant Examiner* — Garrett Atkinson
(74) *Attorney, Agent, or Firm* — Novick, Kim & Lee, PLLC; Jae Youn Kim

(57) ABSTRACT

Provided is a virtual reality indoor bicycle exercise system using a mobile device, which includes a cycle unit; a main controller controlling a load granted to the cycle unit and collecting information on various sensors attached to the cycle unit; a mobile device accessing the main controller to provide information such as physical exercise resistance, and the like and generated in an actual traveling path and receiving exercise information generated by various sensors from the main controller; and a main server wirelessly communicating with the mobile device and storing, updating and managing user information, exercise amount information, and the like.

3 Claims, 11 Drawing Sheets

(51) Int. Cl.

| | |
|---|---|
| *A63B 24/00* | (2006.01) |
| *G06Q 50/22* | (2012.01) |
| *G06Q 10/06* | (2012.01) |
| *A63B 21/00* | (2006.01) |
| *A63B 21/22* | (2006.01) |
| *A63B 23/035* | (2006.01) |
| *H04L 29/08* | (2006.01) |
| *H04L 29/06* | (2006.01) |
| *G01S 19/19* | (2010.01) |
| *G06F 3/01* | (2006.01) |
| *G06F 19/00* | (2011.01) |
| *A63B 21/015* | (2006.01) |
| *A63B 21/055* | (2006.01) |
| *A63B 71/06* | (2006.01) |
| *H04M 1/725* | (2006.01) |

(52) U.S. Cl.
CPC ...... *A63B 21/4034* (2015.10); *A63B 21/4035* (2015.10); *A63B 22/0605* (2013.01); *A63B 23/03516* (2013.01); *A63B 71/0622* (2013.01); *G01S 19/19* (2013.01); *G06F 3/011* (2013.01); *G06F 19/3481* (2013.01); *G06Q 10/0639* (2013.01); *G06Q 50/22* (2013.01); *H04L 67/306* (2013.01); *H04L 67/38* (2013.01); *A63B 21/0051* (2013.01); *A63B 21/015* (2013.01); *A63B 21/0552* (2013.01); *A63B 2022/0611* (2013.01); *A63B 2022/0641* (2013.01); *A63B 2024/009* (2013.01); *A63B 2024/0093* (2013.01); *A63B 2024/0096* (2013.01); *A63B 2071/065* (2013.01); *A63B 2071/0638* (2013.01); *A63B 2220/17* (2013.01); *A63B 2220/20* (2013.01); *A63B 2220/34* (2013.01); *A63B 2220/51* (2013.01); *A63B 2220/64* (2013.01); *A63B 2225/09* (2013.01); *A63B 2225/093* (2013.01); *A63B 2225/50* (2013.01); *A63B 2230/06* (2013.01); *H04M 1/72527* (2013.01)

(58) Field of Classification Search
CPC .......... A63B 21/4034; A63B 23/03516; A63B 22/0605; A63B 2071/0638; A63B 2022/0641; A63B 2220/34; A63B 2220/51; A63B 21/0051; A63B 2230/06; A63B 2071/065; A63B 2220/17; A63B 2220/20; A63B 21/015; A63B 2220/64; A63B 2225/09; A63B 2225/093; A63B 2225/50; A63B 21/0552; A63B 2024/009; A63B 2022/0611; A63B 2024/0096; A63B 2024/0093; A63F 13/00–13/98; G06Q 10/0639; G06Q 50/22; G01S 19/19; G06F 3/011; G06F 19/3481

USPC .............................................. 482/1–9, 51–65
See application file for complete search history.

(56) References Cited

U.S. PATENT DOCUMENTS

| | | | | |
|---|---|---|---|---|
| 4,082,265 | A * | 4/1978 | Berkes | A63B 22/16 280/293 |
| 4,750,737 | A * | 6/1988 | Smith | A63B 69/16 434/61 |
| 5,240,417 | A * | 8/1993 | Smithson | A63B 21/00181 348/121 |
| 5,662,559 | A * | 9/1997 | Vasquez | A63B 22/16 434/61 |
| 6,126,571 | A * | 10/2000 | Parks | A63B 69/16 434/247 |
| 6,126,577 | A * | 10/2000 | Chang | A63B 26/003 434/61 |
| 7,326,151 | B2 * | 2/2008 | Peterson | A63B 22/16 482/57 |
| 7,682,286 | B2 * | 3/2010 | Badarneh | A63B 26/003 482/4 |
| 2002/0055422 | A1 * | 5/2002 | Airmet | A63B 22/16 482/61 |
| 2004/0053751 | A1 * | 3/2004 | Pizolato | A63B 22/16 482/61 |
| 2005/0209064 | A1 * | 9/2005 | Peterson | A63B 22/16 482/61 |
| 2013/0130798 | A1 * | 5/2013 | Nir | A63F 13/803 463/36 |
| 2015/0290490 | A1 * | 10/2015 | Badarneh | A63B 22/0023 482/6 |

FOREIGN PATENT DOCUMENTS

| | | |
|---|---|---|
| KR | 10-2010-0082823 A | 7/2010 |
| KR | 10-1258250 B1 | 4/2013 |
| KR | 10-2013-0090221 A | 8/2013 |
| KR | 10-2013-0097212 A | 9/2013 |

\* cited by examiner

VIRTUAL REALITY INDOOR BICYCLE EXERCISE SYSTEM USING MOBILE DEVICE

TECHNICAL FIELD

The present invention relates to a virtual reality indoor bicycle exercise system using a mobile device, and more particularly, to a virtual reality indoor bicycle exercise system using an enhanced mobile device, which can acquire an interest and a fun as well as muscle exercise by creating the substantially same situation as riding a bicycle on an actual road as a bicycle driving situation including a slope of a road, and the like included in actual GPS route information displayed on a screen is implemented and store and manage an exercise history of a user through the Web to accurately check the amount of exercise and an exercise situation of the user and be easily and conveniently accessed.

BACKGROUND ART

Today, interests of modern people in health management and figure management have increased.

In particular, modern people are interested in supply of social sports at a national level in order to reduce medical cost by entering an aging era.

As a result, there is a trend that people that regularly take exercise increase, but indoor sports which can show an exercise effect within a short time are preferred due to temporal and spatial limits that people have for busy modern life.

In the case of the indoor sports, since the exercise is performed outdoors, the indoor sports can be performed regardless of seasonal and temporal limits and with the increase of people who enjoy the indoor sports, indoor exercise equipments capable of increasing exercise effects have variously developed and supplied.

For example, since bicycle riding does not give an impact on a knee joint and provides a superior exercise effect, the bicycle riding is one of most generalized exercises. Indoor bicycle exercise equipments have been sold in order to acquire the exercise effect and supplied and used in general households as well as public exercise facilities in recent years.

However, since the indoor bicycle exercise equipments are fixed, the indoor bicycle exercise equipments are very monotonous while taking exercise. Therefore, the indoor bicycle exercise equipments cannot satisfy a long-time exercisable desire.

Accordingly, Korean Patent Unexamined Publication No. 2010-0082823 discloses an example that the indoor bicycle exercise equipment can be inclined horizontally to grant a feel as if actually riding the bicycle, thereby exciting a curiosity, providing a fun, and doubling the exercise effect.

However, the disclosed unexamined patent has a structure in which a post part fixing a handle just pivots and a bicycle body is configured to be inclined while the handle post rotates horizontally around the pivot, and as a result, the structure is completely different from a bicycle movement and the exercise effect when stepping on a pedal while standing up with spacing a hip from a saddle in an actual bicycle, thereby degrading a sense of reality.

Meanwhile, bicycle exercise equipments are continuously developed, which can give the feel as if actually riding the bicycle while systematically managing an exercise situation of a user who uses the bicycle exercise equipments and as one of the developed bicycle exercise equipments, Korean Patent Unexamined Publication No. 2013-0090221 is disclosed, which implements a virtual reality bicycle riding exercise function.

However, the examined patent does not have a function to precisely control an actual physical exercise load depending on a stored path and cannot but have a limit in the exercise effect due to restriction of an interesting game function such as a motorcycle type game equipment which can be used in a game center, does not have a management function of individual user histories, and is just disposable, and as a result, it is difficult to systematically manage personal exercise.

In particular, since the bicycle is ridden with only initially stored path information, the user may feel boredom due to repeated use and a system which enables the user to make an exercise plan and take the exercise by using verifying and using exercise information thereof is not provided, and as a result, there is a room for enhancement in terms of convenience, efficiency, and usability.

SUMMARY OF INVENTION

Technical Problem

The present invention is contrived to solve all problems in the related art described above by considering all of the problems and a primary object of the present invention is to provide a virtual reality indoor bicycle exercise system using a new concept of mobile device, which can directly load and use actual bicycle traveling path information to an exercise equipment by using a generalized mobile device, in particular, a smart phone or a tablet, implements a bicycle traveling situation including physical exercise resistance according to a situation of a road shown in a traveling path to enable virtual reality substantially in the same manner as actual road traveling and store an exercise history of a user and easily access and verify the exercise history through the Web, thereby achieving user accessibility that enables easily and conveniently making an exercise plan and analyzing the exercise history by using an indoor bicycle afterwards and furthermore, providing a health care function by analyzing an exercise capability and a health state of the user by using measured heartbeat information.

Solution to Problem

The preset invention as a means for achieving the object provides a virtual reality indoor bicycle exercise system using a mobile device, including: a cycle unit 10 enabling indoor bicycle riding exercise; a main controller MCC controlling a load granted to the cycle unit 10; a mobile device 20 accessing the main controller MCC by using a USB connector or Bluetooth and transmitting information based on traveling path data; and a main server 30 wirelessly communicating with the mobile device 20 and storing, updating, and managing user information and exercise amount information, wherein the cycle unit includes a pair of base frames which are parallel to each other, a main frame installed in the base frame and including a saddle post to which a saddle is fixed and a handle post to which a handle is fixed, an arch-shaped hinge base connecting and fixing the base frames by crossing the base frames, a flake-shaped support bracket fixed to the bottom of the main frame, a frame rotational shaft protruding on the bottom of the support bracket and hinge-fixed to the hinge base, elastic springs of which one end is fixed to the base frame and the other end is fixed to the support bracket, and which are provided at both sides with the hinge base interposed therebetween, respectively, a disk wheel assembled to a rear end of the main frame, a resistor providing resistance force while driving with contacting the disk wheel; and a pedal which is a driving unit installed on the main frame below the saddle to rotate the disk wheel.

According to another preferable feature of the present invention, the system virtual reality indoor bicycle exercise system using a mobile device further includes a user terminal verifying information required for bicycle exercise, which includes an exercise history thereof by accessing a main server.

According to another preferable feature of the present invention, one or more of a shifter controlling the resistor, a heart rate meter measuring heart rate of a user and transmitting the measured heart rate to the mobile device, and a cadence sensor measuring rpm of a crank arm and transmitting the measured rpm to the mobile device is additionally connected to the main controller.

Advantageous Effects of Invention

According to the present invention, a user can take bicycle riding exercise having the same exercise effect of actually taking on a pedal while spacing a hip from a bicycle by horizontal inclination by an elastic spring as virtual reality implemented similarly to an actual GPS traveling path to upsurge an interest and a fun and a device which implements the same gear shift concept as the actual bicycle by software is included together with an up/down switch, and as a result, an exercise load is received differently by using a gear shift according to a capability and an exercise purpose of the user with respect to fixed exercise resistance generated by a slope of a GPS, which is generated in a mobile device when the pedal rotates to maintain improvement of muscular strength and muscular endurance similarly to reality, store, update, and mange exercise information of the user, and easily and conveniently access and read the exercise information anytime through the website, thereby efficiently performing systematic exercise and history management, making an exercise plan, and the like.

DESCRIPTION OF EMBODIMENTS

Figure 1:
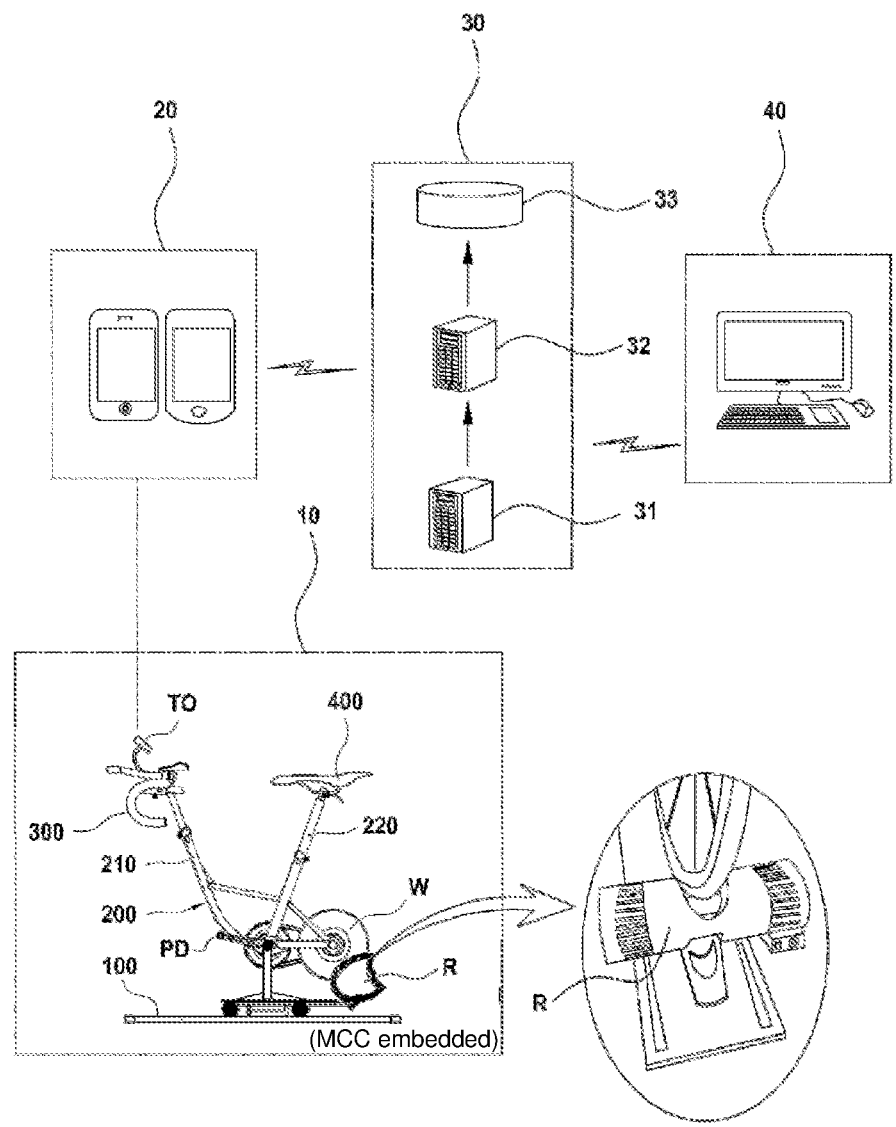
FIG. 1 is an exemplary configuration diagram of a virtual reality indoor bicycle exercise system using a mobile device according to the present invention.

Hereinafter, a preferred embodiment of the present invention will be described in more detail with reference to the accompanying drawings.

Specific structural or functional descriptions of embodiments of the present invention disclosed in the specification are made only for the purposes of describing the embodiments of the present invention, and the embodiments of the present invention may be carried out in various forms, and it should not be construed that the present invention is limited to the embodiments described in the specification.

Further, an embodiment according to a concept of the present invention may have various modifications and various forms and specific embodiments will be illustrated in the drawings and described in detail in the detailed description. However, it is not intended to limit the embodiments according to the concept of the present invention to the specific embodiments, and it will be appreciated that the present invention includes all modifications, equivalences, or substitutions included in the spirit and the technical scope of the present invention.

Figure 2:
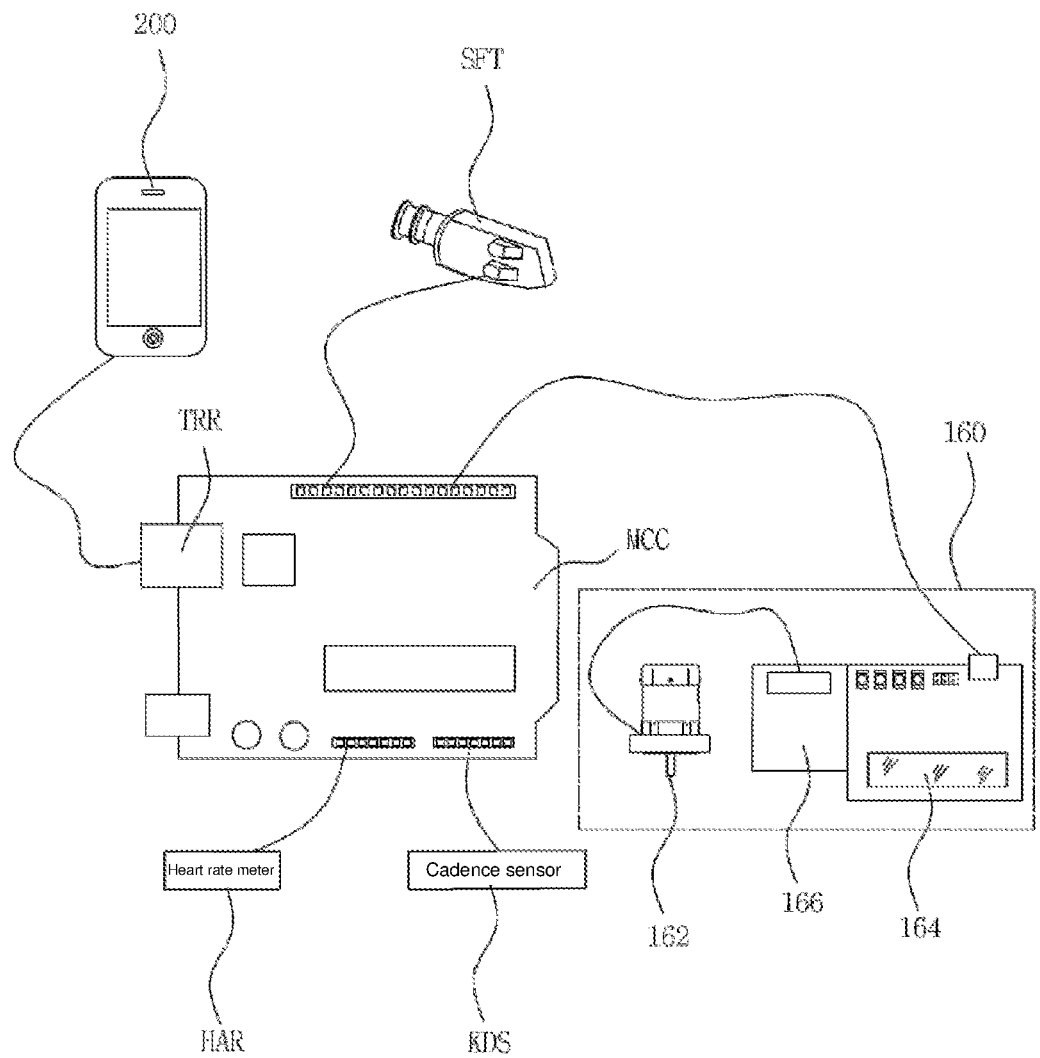
FIG. 2 is an exemplary diagram of a primary module constituting the exercise system according to the present invention.

As illustrated in FIGS. 1 and 2, a virtual reality indoor bicycle exercise system using a mobile device according to the present invention, is configured to include a cycle unit 10; a main controller MCC controlling a load granted to the cycle unit 10 and collecting information on various sensors attached to the cycle unit 10; a mobile device 20 accessing the main controller MCC to provide information such as physical exercise resistance, and the like and generated in an actual traveling path and receiving exercise information generated by various sensors from the main controller MCC; a main server 30 wirelessly communicating with the mobile device 20 and storing, updating and managing user information, exercise amount information, and the like; and a user terminal 40 accessing the main server 30 to verify information required for bicycle exercise, which includes an exercise history thereof.

In this case, the user terminal 40 is optional; therefore, since the mobile device 20, that is, a smart phone itself has been capable of accessing the website in recent years, the mobile device 20 may access the main server 30 without the separate user terminal 40 when passing through only an authentication procedure.

However, when a user verifies and manages an exercise history by accessing the main server 30 through a computer thereof in a home thereof, the user may perform more detailed exercise history analysis and in FIG. 1, the system including even the user terminal 40 is just illustrated by considering that integrated management and exercise program generation may be used.

The mobile device 20 may mean a generally used smart phone or tablet and the user may acquire various information while viewing a screen of the mobile device 20 by attaching the mobile device 20 to a front of the cycle unit 10. That is, various information including a speed, a movement distance, heart rate, power, cadence and an exercise amount may be displayed on the screen of the mobile device 20 in addition to information on the travelling path.

Moreover, the main server 30 may be attached to the cycle unit 10, but the main server 30 is desirably separately present and is substantially a place storing data. To this end, the main server 30 includes any one or more of a web server 31 for the access through the user terminal 40 and a remote procedure call (RPC) server 32 for the access through the mobile device 20 and includes even a database (DB) 33 for storing, updating, managing, and keeping information. For reference, the web server 31 is required only when the user terminal 40 is used.

Figure 3:
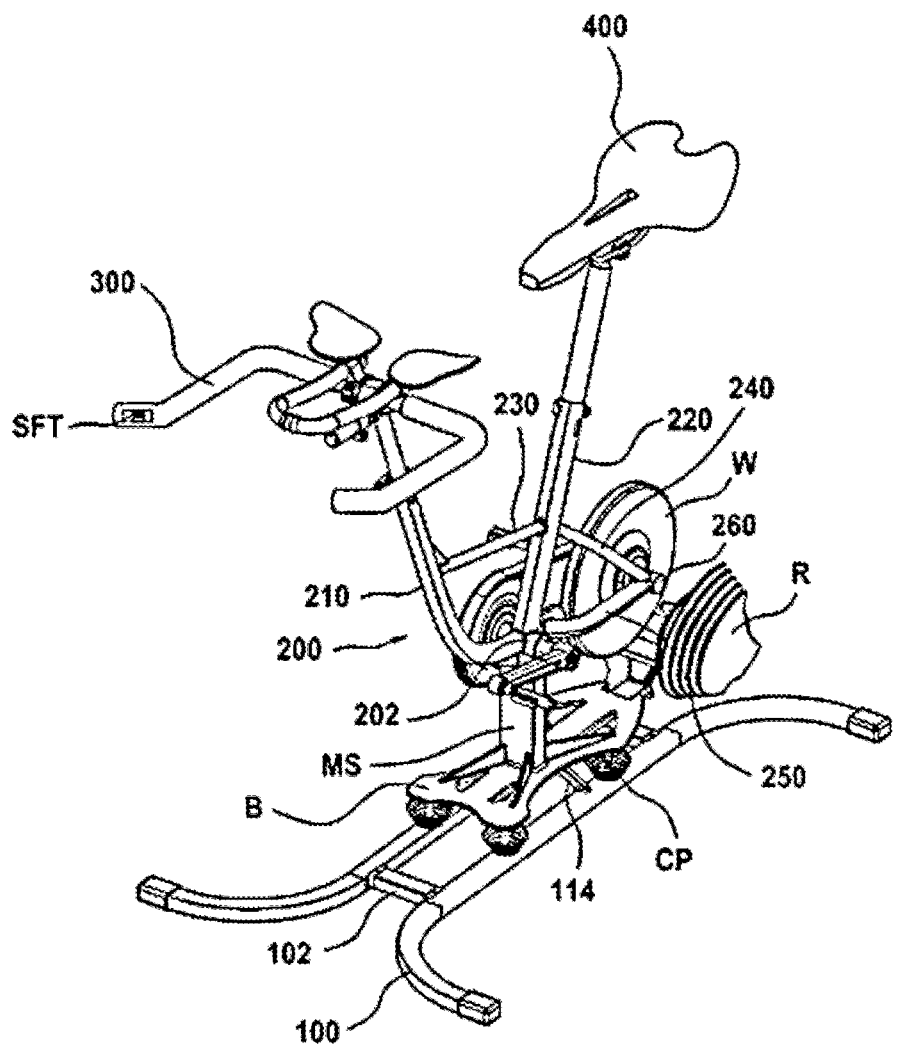
FIGS. 3 to 5 are exemplary perspective views of a cycle module constituting the exercise system according to the present invention viewed at different angles.

Meanwhile, as the cycle unit 10, various types of cycles may be used and examples of the cycles are illustrated in FIG. 3 and the examples are described based on FIG. 3, the cycle unit 10 is configured to include a base frame 100, a main frame 200 assembled to be inclined in left and right directions with respect to the base frame 100, a handle 300 assembled to the top of one-side handle post 210 constituting the main frame 200, a saddle 400 assembled to the other-side saddle post 220 of the main frame 200 so that the user sits with a space with the handle 300, a disk wheel W assembled to a rear end of the main frame 200, a resistor R providing resistance force while being driven by contacting the disk wheel W, and a pedal PD which is a driving unit installed on the main frame 200 below the saddle 400 to rotate the disk wheel W. Herein, the most important part is a function to be inclined in the left and right directions, and as a result, the user may feel an emotion and an exercise effect as if actually riding the bicycle.

In addition, the main controller MCC is provided in the resistor R.

The main controller MCC as a primary control unit for implementing an actual travelling environment is a part that implements an environment such as actual road travelling for the user by implementing road information called from actual GPS path information loaded to the mobile device 20, as illustrated in FIGS. 1 and 2 described above.

The aforementioned resistor R is connected to the main controller MCC. As the resistor R as a part that controls a load, a known resistor such as an electronic resistor may be used or a resistor of a type which is not previously used in the bicycle, such as a resistor using a powder brake may be used.

The electronic resistor R as a module including a motor 162, an electromagnetic brake 164, and a controller 166 makes pedal rotation of the user be difficult by applying magnetic resistance to the electronic resistor R that contacts the disk wheel W based on slopes of an ascent and a descent based on a travelling situation, that is, the road information or allows the disk wheel W to rotate more rapidly by using a motor with respect to the electronic resistor R that contacts the disk wheel to ease a pedal rotation motion on the descend and immediately reflect such a situation, and as a result, the electronic resistor R is controlled by the main controller MCC.

Meanwhile, the powder brake controls torque by changing an array of powder therein by changing a magnitude of a magnetic field of with a change of current and when a powder brake resistor is used, the powder brake resistor is different from the electronic resistor only in that a controller for controlling the change of the current is separately installed and both controls the same as each other in that both controllers are controlled by the main controller MCC in overall.

Further, a USB connection terminal (TRR) and a Bluetooth communication module are provided in the main controller MCC.

The USB connection terminal (TRR) and the Bluetooth communication module provide an interface that may access the mobile device 20 and in some cases, a USB may be directly put and used.

However, in the present invention, only when the mobile device 20 having a wireless communication function of a communication operator, such as WiFi, a desired purpose may be achieved.

In addition, a shifter SFT is also connected to the main controller MCC.

The shifter SFT as a component that electronically implements a concept of a gear shifter just includes only an UP button that increases a gear level and a DOWN button that decreases the gear level and when the shifter SFT is operated, the main controller MCC performs a gear shift concept by controlling an exercise load of the resistor R that contacts the disk wheel W. The shifter SFT may be attached to an appropriate position of the handle 300 by considering convenience of the user, and the like.

Moreover, a heart rate meter HAR and a cadence sensor KDS are further connected to the main controller MCC and the heart rate meter HAR as a chest type heart rate meter stores or displays heart rate while taking exercise as information, the cadence sensor KDS transmits a signal to the mobile device 20 through the main controller MCC by measuring rpm of a crank arm of the pedal to calculate the speed by using a size of a bicycle wheel, which is set by the user, current gear setting information, and the like in the mobile device 20 based on the information and control programs of other apparatuses and mobile applications by using the calculated speed.

Meanwhile, the cycle unit 10 may have a form illustrated in FIGS. 3 to 10 and this is an exemplary matter and a shape of the cycle unit 10 may be modified by considering a design.

For example, the base frame 100 as a base member that supports an indoor bicycle exercise equipment is configured to be stably seated and supported on an installation surface in a structure in which two members having approximately shapes of ⊃ and ⊂ a symmetric structure are parallel and symmetric to each other through being connected and fixed to each other through a connection member 102 so as not to be easily conducted.

Figure 6:
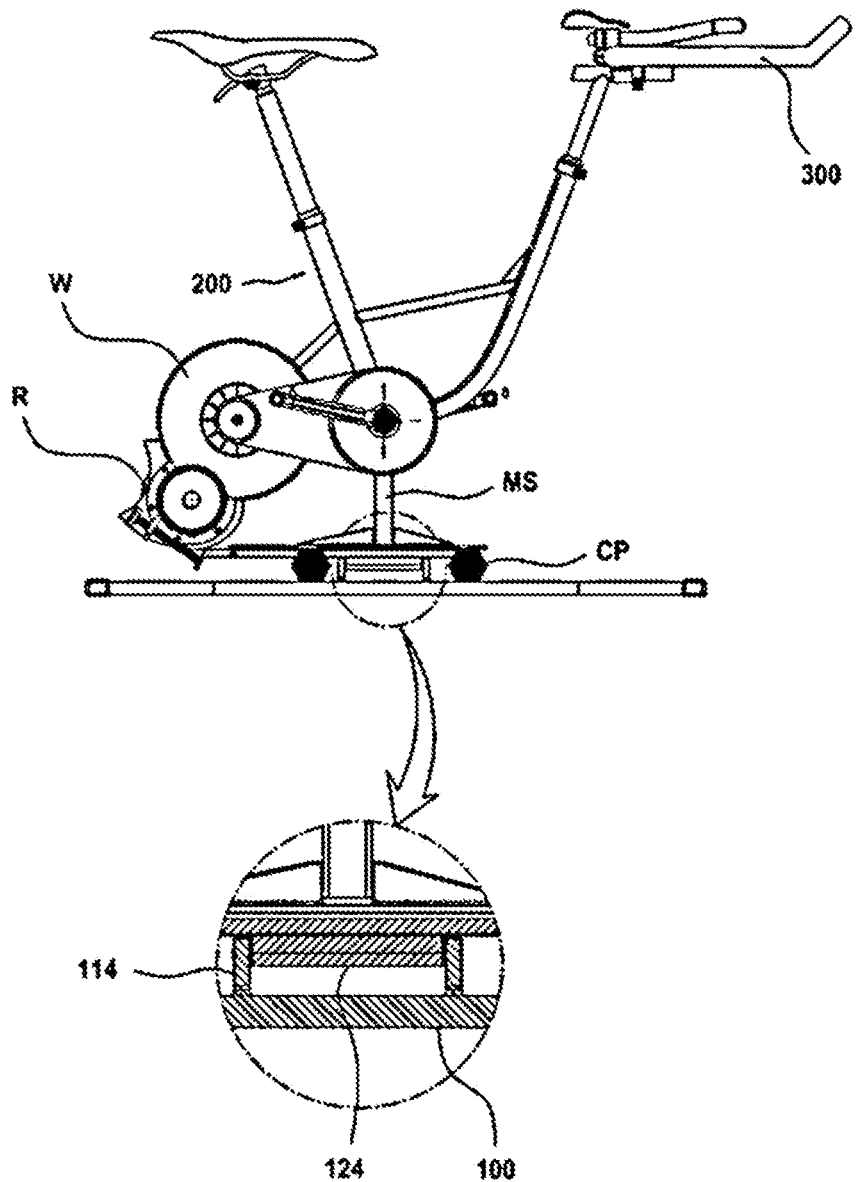
FIG. 6 is a left side view based on FIG. 3.
Figure 8:
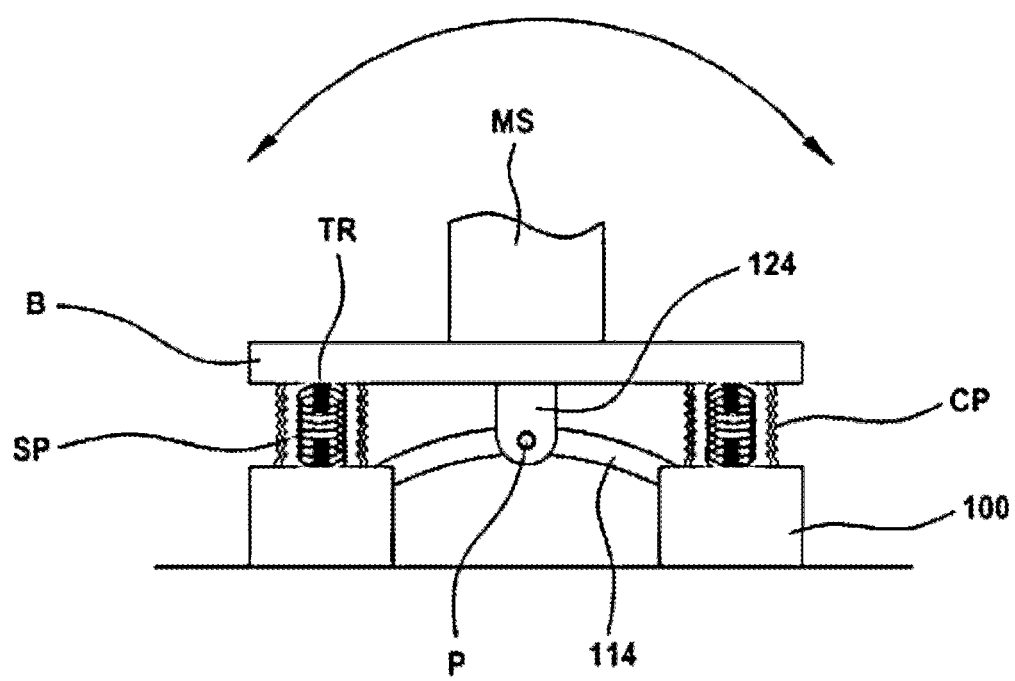
FIG. 8 is an exemplary cross-sectional view illustrating a rotation unit structure constituting exercise equipment according to the present invention.

In addition, a hinge base 114 having a slightly arch shaped by crossing a pair of base frames is solidly fixed onto a longitudinal middle top of the base frame 100 as illustrated in FIGS. 3, 6, and 8 and a frame rotational shaft 124 which is vertically disposed is rotatably fixed to the hinge base 114 through a hinge shaft P.

In this case, the end of the frame rotational shaft 124 may have a 丅 shape and be formed on a single vertical flake such as '1'. However, when the end of the frame rotational shaft 124 has the 丅 shape, stability may be further improved.

Further, a flake-shaped broad support bracket B is provided on the top of the frame rotational shaft 124 and the support bracket B needs to have a width so as to cover a spaced width between the pair of base frames 100.

In addition, a main frame fixation shaft MS is integrally provided on the top of the support bracket B so as to maintain a vertical linear shape to the frame rotational shaft 124 to be maintained to protrude upward.

Moreover, a pair of elastic springs SP is provided at both longitudinal sides of the base frame 100 with the hinge base 114 interposed therebetween and the elastic spring SP is protected by a stretchable protection pipe CP having a corrugated pipe shape.

In this case, one end of the elastic spring SP is fixed to the base frame 100 and the other end is fixed onto the bottom of the support bracket B.

As a result, the main frame fixation shaft MS may be inclined to both left and right sides around the hinge shaft P and since the elastic spring SP is installed, the main frame fixation shaft MS is elastic within a predetermined radius.

Moreover, control projections TR protrude on the bottom of the support bracket B and the top of the base frame 100, which corresponds thereto and while the control projection TR is fixed so as to prevent the elastic spring SR from being left, in particular, the control projection TR fixed to the support bracket B is implemented to control a length in a screw type, and as a result, an inclined angle of the main frame fixation shaft MS may be controlled by varying a range in which the elastic spring SP may be bent.

Therefore, since the user may individually set a rotational angle appropriate thereto, use convenience is increased.

Consequently, when the user pushes the pedal PD while taking off the hip from the saddle 400, the same affect as if actually pushing the pedal while lifting the hip in order to accelerate the bicycle, and as a result, reality is high and the curiosity and the interest are increased, and the resulting exercise effect is also doubled.

In addition, the main frame 200 is fixed to the top of the main frame fixation shaft MS.

Figure 7:
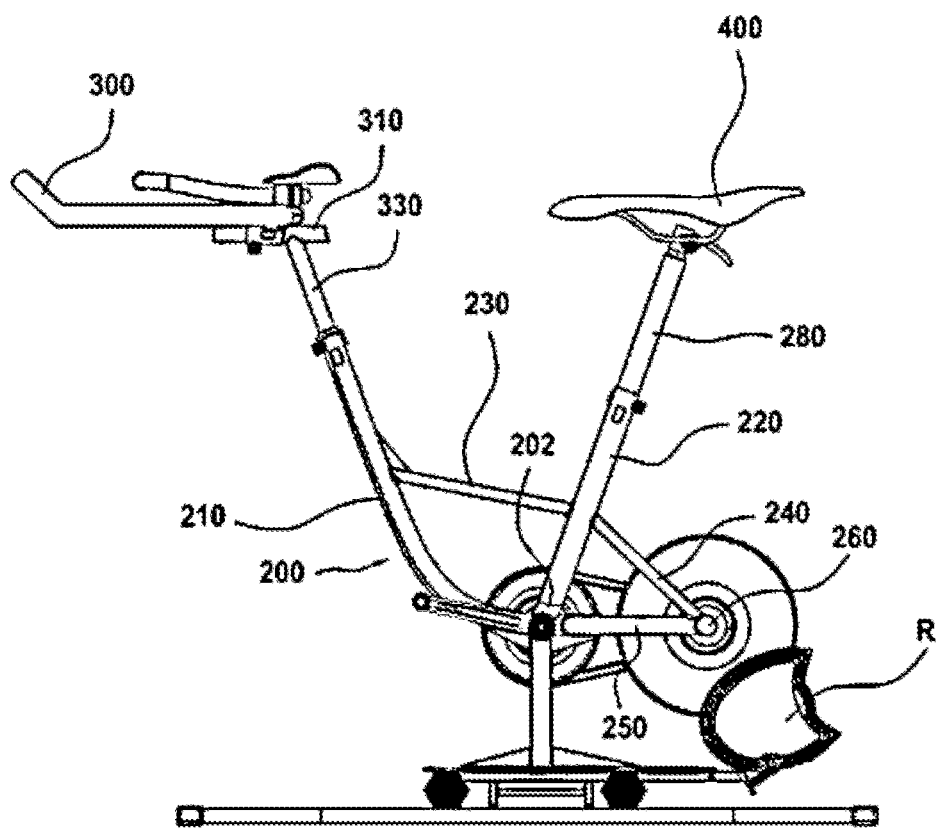
FIG. 7 is a right side view based on FIG. 3.

The main frame 200 is configured to include a handle post 210 to which the handle 300 is fixed around a shaft base 202 in which a pedal shaft fits and a saddle post 220 which extends upward with an interval with the handle post 210 and to which the saddle 400 is fixed and the bottoms of the handle post 210 and the saddle post 220 are joined to the shaft base 202 to constitute one body, as illustrated in FIGS. 3 and 7.

In addition, the handle post 210 and the saddle post 220 are interconnected and restrained through a first connection rod 230 to further increase rigidity, a second connection rod 240 is connected and extended downward in the rear of the saddle post 220, and a third connection rod 250 that extends substantially horizontally meets the end of the second connection rod 240 is joined to a part of the shaft base 202.

Moreover, a wheel shaft base 260 is provided at a point where the second and third connection rods 240 and 250 meet and a wheel shaft of the disk wheel W is rotatably fit and installed in the wheel shaft base 260.

In addition, the resistor R that causes rotational resistance while contacting the disk wheel W is installed on a rear end of the support bracket B and this is described above.

Figure 4:
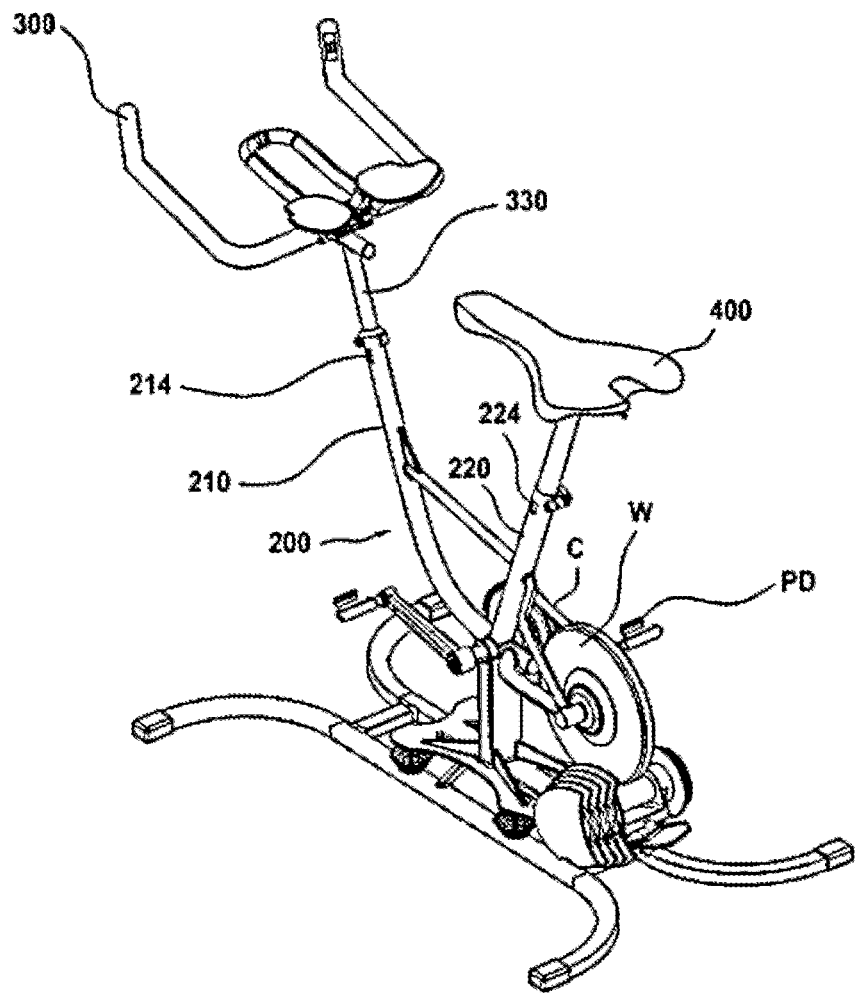

Herein, as illustrated in FIGS. 4 and 7, since a component including the disk wheel W including the pedal PD, a chain C (may be a belt) for driving the disk wheel W, and the like may exclusively adopt a structure of a general bicycle, an additional description thereof will be omitted.

Moreover, in the case of a concept of gear shifting, a signal transferred to an application through the shifter SFT to calculate power appropriate to shifting and the concept of the gear shifting becomes a load of the resistor R and in spite of the same 5% slope, the power is transferred differently according to a gear shifting state.

For example, if the power is 100 when level 5 is set at the slope of 5%, the power becomes 200 when level 1 is set and instead, the pedal needs to be rotated twice in order to progress 5 m at level 5, but the pedal may be rotated only once in order to progress 5 m at level 1.

Figure 5:
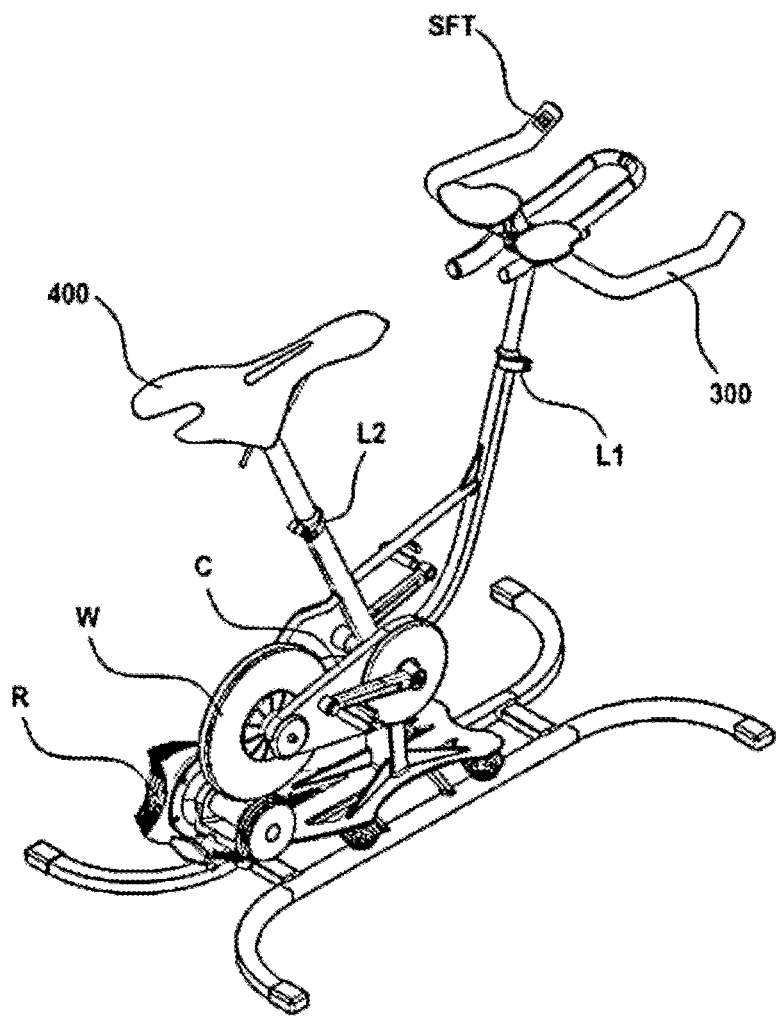
Figure 10:
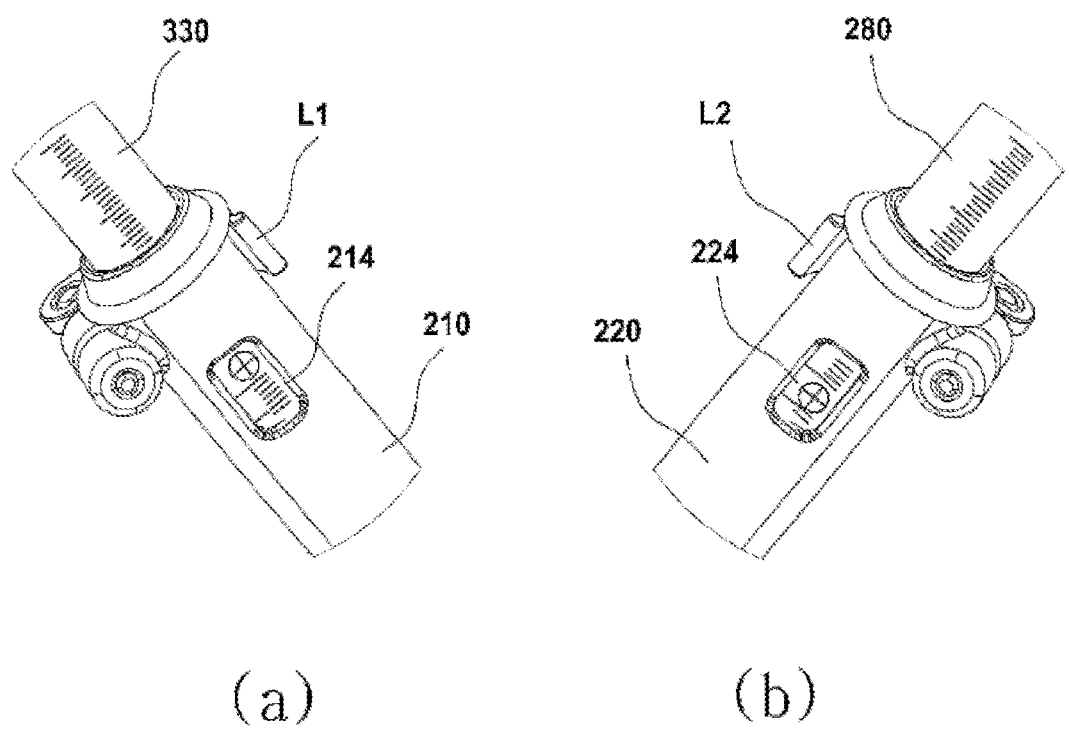
FIG. 10, (a) and (b), shows enlarged diagrams of a primary part illustrating a size control example of a saddle unit constituting the exercise equipment according to the present invention.

In addition, as illustrated in FIGS. 4, 5, and 10, a first display window 214 is formed at one side of the top of the handle post 210 and a second display window 224 is formed at one side of the top of the saddle post 220 and the first display window 214 is a means for reading a scale graven in a longitudinal direction of a stem post 330 which fits in the handle post 210 and the second display window 224 is a means for reading the scale graven in the longitudinal direction in a sit post 280 which fits in the saddle post 220, and as a result, heights of the handle 300 and the saddle 400 may be controlled to be accurately and minutely adjusted to heights appropriate to a figure of the user through the scales.

In this case, the heights of the handle 300 and the saddle 400 are controlled through a separate application and since the application as a means for providing information regarding a height control instructing the height of the saddle 400 and the height of the handle 300 to be adjusted for example, when body information (a height, a weight, an arm length, and the like) of the user is input is a matter implemented through a mobile application of a smart phone, or the like at present, a description of the application itself is omitted.

Moreover, the heights of the saddle 400 and the handle 300 are controlled through QR levers L1 and L2 and the QR levers L1 and L2 are means that easily and rapidly fixes positions commonly as a kind of a lever having a folding structure of a folding type bicycle and is a known component which goes on sale even as a single item.

Figure 9:
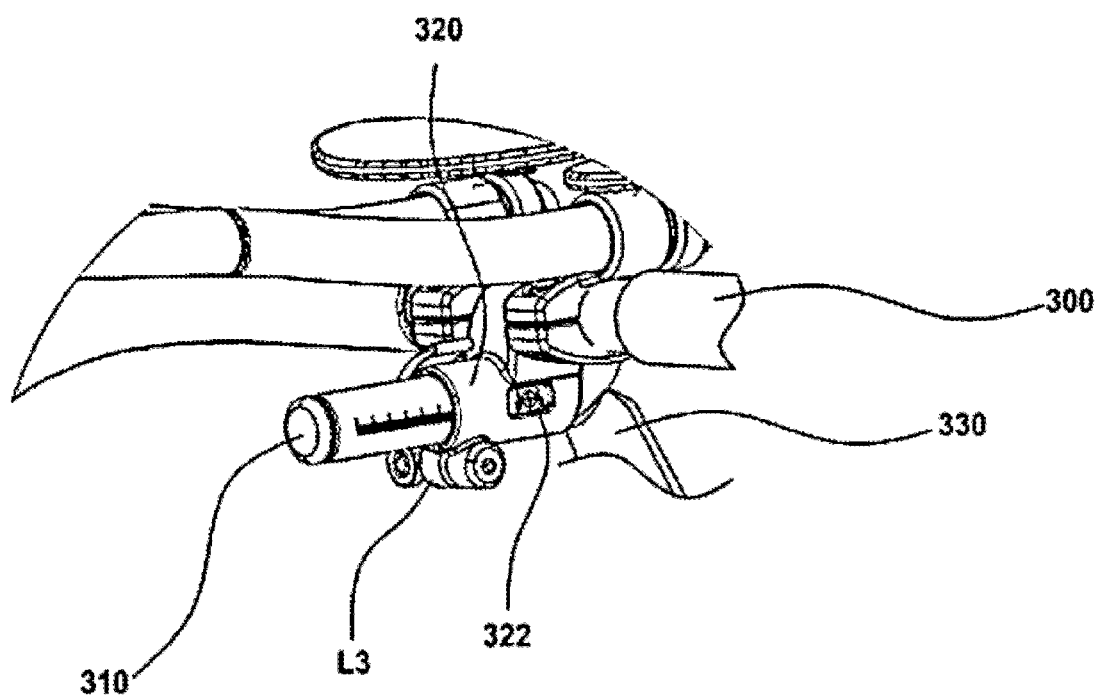
FIG. 9 is an enlarged diagram of a primary part illustrating a size control example of a handle unit constituting the exercise equipment according to the present invention.

Further, as illustrated in FIG. 9, a stem 310 is provided on the top of the stem post 330 substantially in an orthogonal direction, the handle 300 is fixed to the stem 310, a handle joint 320 is provided in the handle 300, and the handle joint 320 fits in the stem 310 to finally fix the handle 300.

In this case, when the scale is formed even in the stem 310 and a third display window 322 is formed in the handle joint 320 which fits in the stem 310, the length may be minutely controlled, and as a result, a distance (depending on an arm length) for each user figure of the handle 300 may also be accurately controlled, thereby inducing a reverse effect of the exercise to be suppressed and accurate exercise to be taken.

In this case, the stem 310 and the handle joint 320 are also fixed through a QR lever L3 described above.

The present invention having the configuration has the following operating relationship.

First, the user precisely controls the heights of the saddle, the handle, and the like according to body information thereof by using a separate application (using a known application of the smart phone, or the like).

Then, the mobile device 20 is connected to the main controller MCC by using a USB connector or Bluetooth and actual path data (GPS data) that is intended to travel is loaded to the mobile application by accessing the main server 30 by using the application installed in the mobile device 20.

Then, the mobile application transmits corresponding information to the main controller MCC in real time by calculating resistance on which the resistor R will act based on information such as the gradient, a distance, and the like of the corresponding path to control the resistor R. That is, in the case of an upward slope, the cycle unit may move only by applying large force by using the electromagnetic brake 164 of the resistor R and in the case of travelling by a downward slope and inertia, the cycle unit is controlled to move only with small force by using the motor 162.

Further, cadence (pedal rpm) information, heart rate meter information, set gear level information, measured while travelling are transmitted to the mobile device 20 under a control of the main controller MCC and the mobile device 20 stores the information in the DB 33 of the main server 30 through an RPC server 32.

In this case, user classification preferably allows a unique identification to be identified and recognized by using an ID set in the mobile application.

The present invention is described below in more detail with reference to a photograph of FIG. 11, which is an implementable example in association with the operation of the present invention.

First, when the application is executed through the mobile device 20 (in particular, a pad) provide on a cradle TO of the handle 300 while the user sits on the exercise equipment, a various mode (program modes, GPS modes, and the like) selection portal screen is shown through a Bluetooth connection/verification process (USB connection is available).

Figure 11:
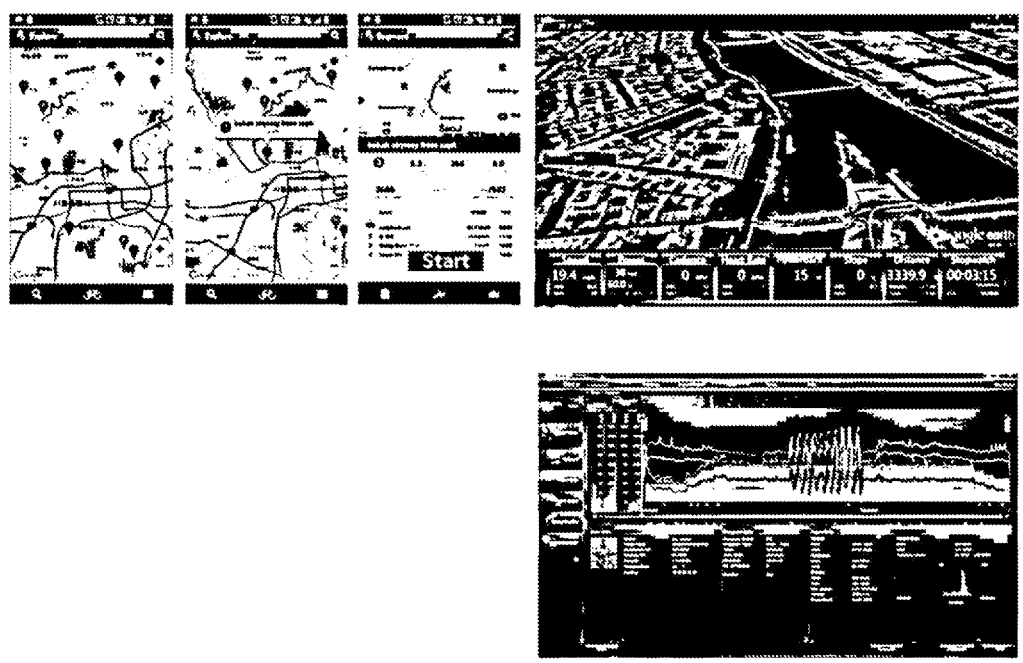
FIG. 11 is an actual implementation screen of the exercise system according to the present invention.

In this case, when the user selects the GPS mode, a map of FIG. 11 is illustrated and a point of interest (POI) is displayed on the map. This means that a place where a GPS path which users upload is displayed and among them, when a desired path is selected, simple information is verified and when the path is selected again, detailed information (an average gradient, an exercise difficulty, a path length, histories of previous users, and the like) is displayed.

When the selection is completed through such a process, the user presses a Start button. Then, an earnest exercise screen is displayed and as illustrated in FIG. 11, exercise information, a coordinate motion in the map, a coordinate motion on the gradient, and the like may be verified realistically.

Moreover, a simple history is verified with the mobile after the exercise, verifying/analyzing an exercise history which is detailed and needs to be analyzed by accessing the main server 300 through the Web is the primary configuration and operation of the present invention.

As described above, since the user actually rides the bicycle while viewing a road situation displayed on an actual screen while reflecting an actual road situation as it is during indoor bicycle riding exercise, the interest and the fun are promoted and the exercise effect is doubled and since various exercise indexes (data) measured during the bicycle riding exercise are stored in the DB 33 as they are, the exercise indexes (data) may be verified by accessing the main server 30 anytime even after the exercise ends and further, subsequent exercise may be planned based on the verified exercise information and health management may be systematically performed, and as a result, availability thereof is very high.

Moreover, in the case of information on a road on which the users will travel, the user may personally upload GPS log data (generatable in an extant bicycle tracking application) generated during actual bicycle traveling, and as a result, the user may take exercise according to an exercise plan without a temporal or environmental limit by considering a desired exercise path and various road information uploaded by another user removes a spatial limit to travel by selecting a world famous bicycle course and double an element of virtual reality by developing a program including a road image afterwards. Further, when the user personally designs an environment (the gradient and the distance) where the user will take exercise by using the Web installed in the mobile device 20 or a Web program through the user terminal as well as the exercise using the actual road information and thereafter, the information is transmitted to the main controller MCC, the user may take desired exercise, and as a result, the exercise effect may be further promoted and muscular strength at a desired portion may be reinforced.

The invention claimed is:

1. A virtual reality indoor bicycle exercise system using a mobile device, the system comprising:
   a cycle unit enabling indoor bicycle riding exercise;
   a main controller controlling a load granted to the cycle unit;
   a mobile device accessing the main controller by using a USB connector or using a wireless protocol, and transmitting information based on traveling path data; and
   a main server wirelessly communicating with the mobile device and storing, updating, and managing user information and exercise amount information,
   wherein the cycle unit includes:
   a pair of base frames which are parallel to each other,
   a main frame installed in the base frames and including a saddle post to which a saddle is fixed and a handle post to which a handle is fixed,
   an arch-shaped hinge base connecting and fixing the base frames by crossing the base frames,
   a flake-shaped support bracket fixed to a bottom of the main frame,
   a frame rotational shaft protruding on a bottom of the support bracket and hinge-fixed to the hinge base,
   two elastic springs connected between the base frames and the support bracket, one end of one of the two elastic springs connected to one of the base frames, one end of the other of the two elastic springs connected to the other of the base frames, and the other end of each of the two elastic springs connected to the support bracket,
   a disk wheel assembled to a rear end of the main frame,
   a resistor providing resistance force while driving with contacting the disk wheel; and
   a pedal which is a driving unit installed on the main frame below the saddle to rotate the disk wheel.

2. The virtual reality indoor bicycle exercise system of claim 1, further comprising:
   a user terminal verifying information required for bicycle exercise, which includes an exercise history thereof by accessing a main server.

3. The virtual reality indoor bicycle exercise system of claim 1, further comprising one or more of a shifter controlling the resistor, a heart rate meter measuring a heart rate of a user and transmitting the measured heart rate to the mobile device, and a cadence sensor measuring rpm of a crank arm and transmitting the measured rpm to the mobile device and additionally connected to the main controller.

* * * * *